United States Patent
Bleyer et al.

(10) Patent No.: US 8,722,911 B2
(45) Date of Patent: May 13, 2014

(54) PROCESS AND METHOD FOR IMPROVING THE WATER REUSE, ENERGY EFFICIENCY, FERMENTATION, AND PRODUCTS OF AN ETHANOL FERMENTATION PLANT

(71) Applicants: James Robert Bleyer, Maumee, OH (US); Thomas J Czartoski, Tecumseh, MI (US); Puneet Chandra, Ann Arbor, MI (US)

(72) Inventors: James Robert Bleyer, Maumee, OH (US); Thomas J Czartoski, Tecumseh, MI (US); Puneet Chandra, Ann Arbor, MI (US)

(73) Assignee: Valicor, Inc., Dexter, MI (US)

( * ) Notice: Subject to any disclaimer, the term of this patent is extended or adjusted under 35 U.S.C. 154(b) by 0 days.

(21) Appl. No.: 13/870,261

(22) Filed: Apr. 25, 2013

(65) Prior Publication Data

US 2013/0344554 A1 Dec. 26, 2013

Related U.S. Application Data

(60) Provisional application No. 61/662,019, filed on Jun. 20, 2012.

(51) Int. Cl.
*C11B 1/12* (2006.01)

(52) U.S. Cl.
USPC .......... 554/8; 554/9; 127/67; 426/54; 435/99; 435/151

(58) Field of Classification Search
None
See application file for complete search history.

(56) References Cited

U.S. PATENT DOCUMENTS

| | | | |
|---|---|---|---|
| 6,441,208 B2 | 8/2002 | Bijl | |
| 6,727,373 B2 | 4/2004 | Bijl | |
| 7,601,858 B2 | 10/2009 | Cantrell | |
| 7,608,729 B2 | 10/2009 | Winsness et al. | |
| 7,868,195 B2 | 1/2011 | Fleischer | |
| 2008/0188676 A1 | 8/2008 | Anderson | |
| 2008/0299632 A1 | 12/2008 | Winsness | |
| 2009/0093027 A1* | 4/2009 | Balan et al. | 435/99 |
| 2009/0110772 A1* | 4/2009 | Verkade et al. | 426/48 |
| 2012/0102823 A1* | 5/2012 | Hennessey et al. | 44/307 |
| 2012/0110898 A1 | 5/2012 | Malm | |
| 2012/0116105 A1 | 5/2012 | Aaltonen | |

OTHER PUBLICATIONS

Belyea et al. "Composition of corn and distillers dried grains with solubles from dry grind ethanol processing" Bioresource Technology vol. 94: 293-298.*
Minowa, et al. "Oil Production From Buckwheat Stillage By Thermochemical Liquifaction." Journal of Nire, vol. 2, No. 4, p. 53-62. Jul. 26, 1993. Japan. (Abstract).
Agler, et al. "Conversion of Thin Stillage from Corn-to-Ethanol Dry Mills into Biogas to Offset Natural Gas Consumption." Powerpoint presentation, Mar. 7, 2008.

* cited by examiner

*Primary Examiner* — Jon P Weber
*Assistant Examiner* — Teresa E Knight
(74) *Attorney, Agent, or Firm* — Kohn & Associates PLLC

(57) ABSTRACT

A method of processing stillage by hydrothermally fractionating stillage to create unique product fractions, by heating the stillage to a temperature of 250 degrees F. to 350 degrees F., and recovering a stickwater fraction from the stillage. Stickwater, oil, biomass, bio-products, extracts, metabolites, and treated water obtained from the method above. A method of performing ethanol fermentation by hydrothermally fractionating stillage to create unique product fractions by heating the stillage to a temperature of 250 degrees F. to 350 degrees F., separating the stillage into a ProFat fraction and a stickwater fraction, and recovering oil from the ProFat fraction.

15 Claims, 11 Drawing Sheets

FIGURE 1 – PRIOR ART

PROCESS AND METHOD FOR IMPROVING THE WATER REUSE, ENERGY EFFICIENCY, FERMENTATION, AND PRODUCTS OF AN ETHANOL FERMENTATION PLANT

BACKGROUND OF THE INVENTION

1. Technical Field

The present invention relates to methods of ethanol fermentation. More specifically, the present invention relates to processing stillage.

2. Background Art

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

Ethanol fermentation is the biological process by which sugars are converted into ethanol and carbon dioxide through yeast fermentation. Corn is one of the main feedstock materials used to produce ethanol. Dry milling has previously been used to produce ethanol from corn on other starch sources through fermentation (shown generally in FIG. 1, labeled "Prior Art"). Corn is milled to a flour, slurried, and treated with enzymes to convert the starch to sugars. The sugars are converted to ethanol in large fermenters. The ethanol is recovered through a distillation process. The residual spent grain, referred to as whole stillage, contains corn germ, corn bran, corn oil, unconverted starch, unfermented sugars, yeast cells, yeast metabolites, and other suspended and dissolved solids. The whole stillage stream is generally separated into wet distillers grain (WDG) and thin stillage. The wet distillers grains can be dried to produce Dry Distillers Grain (DDG). A portion of the thin stillage, referred to as backset, is recycled to the front end of the ethanol process as make up water. The remaining thin stillage is evaporated to a syrup, added to the wet distillers grains and dried as Dried Distillers Grains with Solubles (DDGS). WDG, DDG, and DDGS are important co-products that are critical to the economic viability of the ethanol process. However, their value can be enhanced by extracting more valuable co-products from these streams. It has only recently been a goal to recover additional materials from the co-products for further use.

Materials, such as oil, protein, and other solubles, in the whole stillage are very valuable; however, recovery has shown to be inefficient and uneconomical. Recently, various methods have been attempted to recover the additional materials from stillage. These methods include traditional separation techniques such as heating the stillage stream and performing evaporation, using centrifugation, or using membrane filtration, in order to recover these additional materials. The result of each of these separation processes on stillage is a concentrate and a water phase wherein most of the solids have been removed.

U.S. Patent Application Publication No. 2009/0250412 and U.S. Pat. No. 7,608,729 to Winsness, et al., disclose methods for recovering oil from stillage including oil resulting from a process used for producing ethanol from corn. Winsness, et al. generally believe that filtration increases operating costs and therefore focus on separation by heating. In one embodiment, the method includes heating the stillage to a temperature sufficient to at least partially separate, or unbind, the oil therefrom. The heating step includes heating to a temperature above 212 degrees F. but less than about 250 degrees F. The method also includes the step of pressurizing the heated stillage to prevent boiling. The method further includes recovering the oil from the stillage using a gravity separation process including centrifugation. While oil can be recovered from this method there are many products in the thin stillage that are not recovered. For example, the process disclosed by Winsness et al. does not include recovery of stickwater and ProFat fractions (as defined below) and alternative uses for stickwater. Furthermore, it is generally accepted in the art that heating the thin stillage to higher than 250 degrees F. is harmful to proteins and other biological components.

U.S. Pat. No. 6,106,673 to Walker discloses a process and system for the separation of a fermentation process byproduct into its constituent components and for the subsequent recovery of those constituent components. The process requires 1) heating of a mixture containing the byproduct so as to separate the oil from a base component of the byproduct to which the oil is bound at a temperature from about 140 degrees F. to about 250 degrees F., followed by 2) recovering the base product, oil, and possibly other substances such as molasses from the mixture. The process can be performed on a large scale and in a continuous fashion using a mechanical separator to recover fibers from a heated mixture to produce a solids stream and a liquor stream and by then removing oil and insoluble substances from the liquor stream in an evaporator assembly. Energy consumption and water consumption are minimized through 1) the use of waste heat from the system's dryer as an energy source for the evaporator assembly and 2) the use of condensed liquids from the evaporator assembly to dilute the mixture. Fibers recovered during the process can be dried efficiently in a way that produces a superior product.

U.S. Pat. No. 5,250,182 to Bento, et al. discloses a stepwise membrane separation process to recover lactic acid and glycerol, together from thin stillage in an ethanol stream. In each step, the permeate recovery is at least 50%. In a first step, an ultrafiltration (UF) membrane means produces a UF permeate stream in which not only essentially all the insoluble portion of the thin stillage greater than about 0.005 µm is removed as UF concentrate, but also at least 50% of solubles having a molecular weight $>2\times10^5$ Daltons, including dissolved proteins in the thin stillage. In a second step to which the UF permeate is fed, a nanofiltration (NF) membrane produces a NF permeate with a rejection of less than 30% of both the lactic acid and the glycerol, preferably less than 25%. Essentially all molecules larger than lactic acid or glycerol are removed in the NF concentrate. In a third step, to which the NF permeate is fed, a reverse osmosis (RO) membrane means produces demineralized RO water which contains essentially no lactic acid and glycerol, because these are rejected in the RO concentrate. Use of the membrane separation process in the production of ethanol based on the dry-milling of corn, eliminates the use of a conventional evaporator.

While heating and filtration described in prior art provides some separation of co-products, recovery is limited and costs remain high. One advantage of the present invention is that hydrothermal fractionation of stillage produces a physico-chemical alteration, which enables a facile separation allowing for improved recovery of co-products. With respect to the present invention, "hydrothermal fractionation" means heating a substantially aqueous stillage stream to a temperature within a prescribed temperature range, and holding at temperature for a period of time within a prescribed residence time range. A saturation pressure is established and maintained during the hydrothermal fractionation step. Physico-chemical alteration means that both physical and chemical changes are imparted to the stillage by the hydrothermal fractionation step. Manifest physical changes include changes in the rate of phase separation, live phase volumetric fractions and phase densities, phase hydrophobicity and changes in color or appearance. Chemical changes include changes in the distribution of protein, fat (oil) and carbohydrate (fiber) components between the substantially liquid phase and the substantially solids phase. These physical and chemical changes are mutually dependent and hence the term physicochemical is applied.

By analogy, thermal hydrolysis has been investigated as a pretreatment step prior to anaerobic digestion of biomass, in particular the anaerobic digestion of waste activated sludge from biological waste water treatment facilities and the pretreatment of cellulosic biomass prior to enzymatic hydrolysis to liberate cellulosic sugars. The former has been commercially implemented while the latter remains a research and development endeavor. Camacho et al. (*Combined experiences of thermal hydrolysis and anaerobic digestion—latest thinking on thermal hydrolysis of secondary sludge only, for optimum dewatering and digestion.* Proceedings of the WEFTEC® 2008 Conference, Chicago, Ill. Water Environment Federation) reviewed the use of thermal hydrolysis as a pretreatment to anaerobic digestion of activated sludge and noted the improvements in both sludge dewaterability and biogas yield during anaerobic digestion. Optimal treatment temperatures were generally in the range of 150-200° C. (302-392° F.).

Yu et al. (*Some Recent Advances in Hydrolysis of Biomass in Hot-Compressed Water and Its Comparisons with Other Hydrolysis Methods*, Energy & Fuels 2008, 22, 46-60) reviewed the use of hot compressed water (HCW) as a pretreatment for biomass in the production of cellulosic biofuels. The authors focused on the unique physicochemical properties of HCW and the chemistries imparted by HCW as well as the yield of fermentable sugars resulting from enzymatic hydrolysis of the pretreated biomass.

Kim et al. (including Ladisch) (*Enzyme hydrolysis and ethanol fermentation of liquid hot water and AFEX pretreated distillers' grains at high-solids loadings*, Bioresource Technology 99 (2008) 5206-5215.) investigated the thermal hydrolysis of dry grind ethanol DDGS as a cellulosic pretreatment prior to enzymatic hydrolysis of the cellulosic biomass. The objective of the thermal treatment of Kim et al. was to prepare the cellulose of DDGS for downstream enzymatic hydrolysis to glucose by cellulase and beta-glucosidase enzymes. U.S. Pat. No. 5,846,787 to Ladisch et al. claims use of thermal hydrolysis in the range of 160-220° C. (320-428° F.) as a pretreatment for cellulosic biomass prior to enzymatic treatment with cellulase. To our knowledge, the hydrothermal fractionation treatment of the present invention has not been described in patents or literature as a means to thermally fractionate stillage and produce enhanced stickwater and ProFat fractions thereof in conventional dry-grind corn ethanol plants.

While heating has also been performed as described in the prior art for recovery of corn oil, the processes that use heating have not used a temperature range which causes this physicochemical alteration. The hydrothermal fractionation and induced physicochemical alteration also results in a set of products obtained from the stillage that are not obtainable with the processes described above, providing an economic advantage.

Prior art processes have tried to remove different solids from thin stillage with: a) anionic polymer additives to increase coagulation and precipitation (Hughes, U.S. Pat. No. 8,067,193), b) the use of microfiltration and subsequent ultra-filtration (Prevost, et. al., US 2004/0082044 A1), c) treatment with polyacrylamide and electrocoagulation (Griffith, US 2007/0036881 A1), d) multiple solvent extraction and filtration steps to recover organic solvent soluble solids from the thin stillage. Other prior art processes have described removal of solids from the clarified aqueous phase through the use of filters after separation of concentrated thin stillage into a light oil phase and a heavy aqueous phase (Woods, et. al., US 2011/0275845 A1). And other prior art processes describe separating solids from a processed broth through chemical reaction to increase the water solubility of insoluble cellulosic, melaninic, ligninic, or chitinic solids (Verkade, et. al., US 2009/0110772 A1). Other efforts have involved filtration of depleted lignocelluosic fermentation hydrolysate broth (more like whole stillage) to separate undissolved solids from the liquid phase and create a low solids liquid (Hennessey, et. al., US 2012/0178976 A1 and Hennessey, et. al., US 2012/0102823 A1). None of these prior art methods in solid-liquid separation has been shown to have any effect on the production of clarified water to improve the growth of algae, fungi or other microorganisms in the production of biomass, metabolites, bio-products, and/or extracts. In other words, the clarified thin stillage of the prior art has very different properties than the stickwater fraction produced in the present invention, and the stickwater fraction of the present invention is shown to be advantageous as a growth media.

Therefore, there is a need for a method of producing a physicochemical alteration that changes the co-products in the stillage and enables facile separation of co-products from stillage streams in ethanol processing as well as providing streams suitable for improving biological production and recovery of valuable co-products, extracts, metabolites and treated water.

SUMMARY OF THE INVENTION

A method of hydrothermally fractionating stillage to create unique product fractions, by heating the stillage to a temperature of 250 degrees F. to 350 degrees F., and recovering a stickwater fraction from the stillage.

The present invention also provides for oil, stickwater, ProFat, protein meal, biomass, bio-products, extracts, metabolites, and treated water obtained from the method above.

The present invention further provides for a method of performing ethanol fermentation by hydrothermally fractionatating stillage to create unique product fractions by heating the stillage to a temperature of 250 degrees F. to 350 degrees F., separating the stillage into a ProFat fraction and a stickwater fraction, and recovering oil from the ProFat fraction.

The present invention provides for a method of performing ethanol fermentation by separating whole stillage into stillage and wet cake, hydrothermally fractionating the stillage to create unique product fractions by heating the stillage to a temperature of 250 degrees F. to 350 degrees F., separating the stillage into ProFat and stickwater fractions, recovering oil, recovering a first stickwater fraction and a ProFat fraction, dewatering the ProFat fraction, obtaining a dewatered ProFat fraction and a second stickwater fraction, and adding the second stickwater fraction to the first stickwater fraction, and further processing the first and second stickwater fractions by a process selected from the group including biological processing and chemical processing, and using the first and second stickwater fractions as growth media in the processing step.

DESCRIPTION OF THE DRAWINGS

Other advantages of the present invention are readily appreciated by reference to the following detailed description when considered in connection with the accompanying drawings wherein:

FIG. 8 also includes photographs of centrifuge tubes to illustrate the facile separation of hydrothermally fractionated stillage under low-g separation.

DETAILED DESCRIPTION OF THE INVENTION

Figure 1:
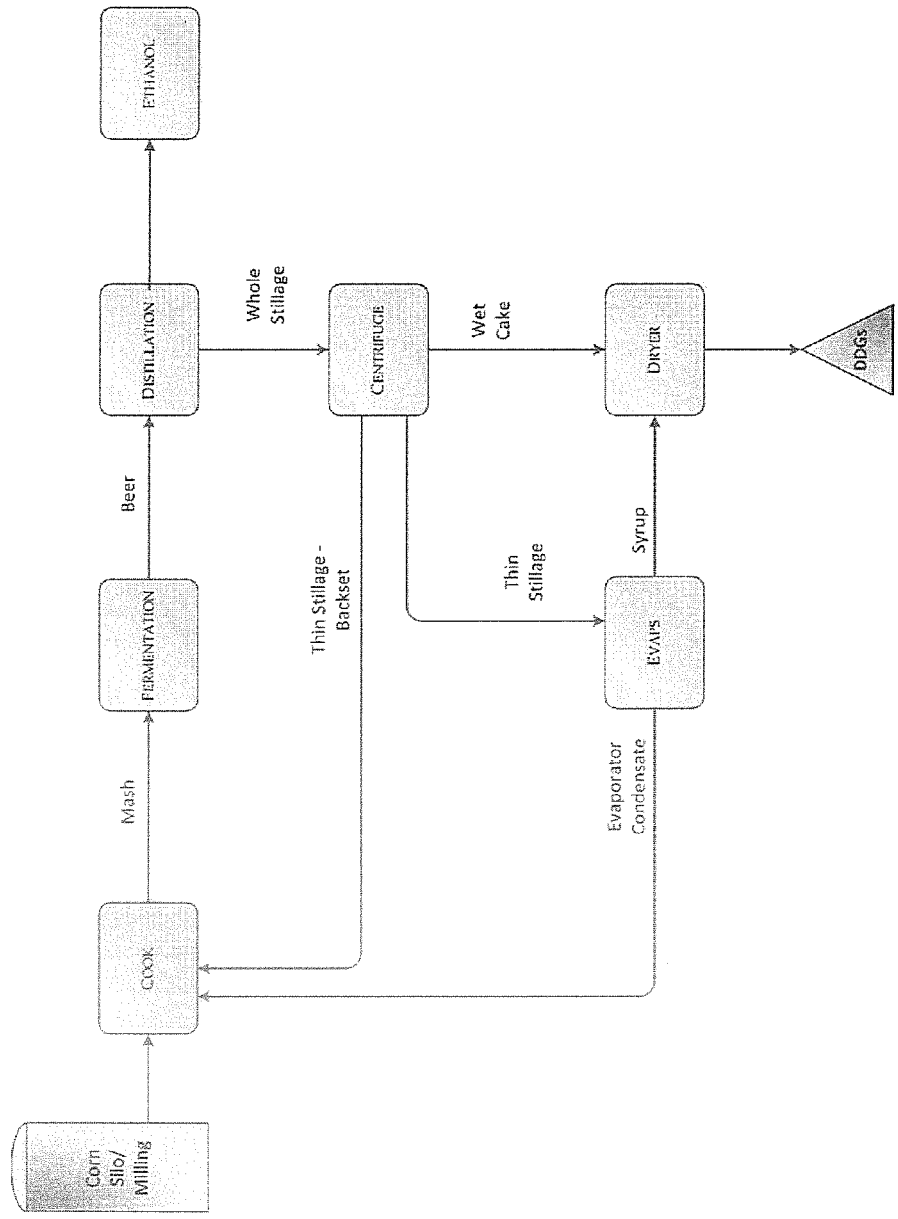
FIG. 1 is a flowchart of a prior art ethanol fermentation process.

Most generally, the present invention provides for methods of ethanol fermentation that include processing of stillage to improve the overall fermentation process and generate useful products. The present invention provides for a method of processing stillage by hydrothermal fractionation of the stillage to enable facile separation and create unique product fractions by heating the stillage to a temperature of 250 degrees F. to 350 degrees F. The present invention further provides for methods of physicochemical alteration of stillage and recovering a stickwater fraction and a ProFat fraction that are chemically different than stickwater and ProFat fractions in the prior art.

"Stillage" as used herein, refers to a cloudy liquid produced during ethanol fermentation that includes solids that are not fermentable, solubles, oils, organic acids, salts, proteins, and various other components. In the current ethanol production process, the suspended solids in thin stillage limit the effectiveness of the evaporators and decrease the efficiency of the fermentation process.

"Stickwater" as used herein, refers to a fraction of the stillage stream that is generally very low in suspended solids, typically less than 1 wt % or less than 50% of the suspended solids in conventional thin stillage, and is mainly water and solubles. This term is also further described below.

"ProFat" as used herein, refers to a fraction of the stillage stream that contains both proteins (including protein meal) and fats (including corn oil and other oils) as well as other solids. This term is also further described below.

In the prior art, thin stillage is either evaporated and added to dried distiller grains or recycled as backset to the front end of the process. The suspended solids in the portion of the thin stillage that is evaporated cause fouling. The evaporators must be oversized to account for this fouling. The evaporators must be taken off-line from time to time for cleaning. This adds to the capital cost and operating cost of an ethanol plant.

Thin stillage used as backset is less than ideal for that purpose. The suspended solids present in backset limits the amount of corn that can be added during the slurry process. Because of the non-fermentable solids in the backset, pumps, heat exchangers, and fermenters must be oversized, increasing the capital cost and operating cost of the process. Furthermore, the suspended solids in the stillage can interfere with the utilization of nutrients during fermentation.

Thin stillage used as backset is also less than ideal because the thin stillage contains glycerol, organic acids and other yeast metabolites. These compounds act as fermentation inhibitors, slowing fermentation and decreasing throughput.

Using thin stillage as backset does have some advantages. The soluble proteins from the corn and dead yeast cells act as nutrients, however, insoluble proteins cannot be utilized. Ethanol plants will operate the stillage centrifuge to maximize overall plant efficiencies which results in thin stillage typically in the range of 1.5%-3% suspended solids (4%-6% total solids). Preferably, when thin stillage is used herein, it has 4% or less suspended solids. However, the stillage processing method of the present invention creates low solids stickwater that avoids the operational issues associated with higher solids. Processing stillage with higher solids as compared to thin stillage obtained from the current conventional process has advantages. It is known that oil is bound to the suspended solids in stillage. By manipulating the solids content of stillage, the present invention can produce a desired protein and oil yield. Processing stillage with higher solids content can also produce a stickwater that is more suitable for use as a fermentation media, increasing ethanol titer. Therefore, the stillage that is processed in the method herein can be whole stillage, containing approximately 8-10% suspended solids (11-13% total solids) or a stillage where the total suspended solids are reduced to a level below whole stillage, including reducing solids to the level of thin stillage. Stillage with a suspended solid content less than whole stillage and more than thin stillage is referred to as thick stillage. Thick stillage can have approximately 3 to 8% suspended solids, and preferably between 4 to 8% suspended solids. The solids separation can be done in one or more steps.

In the method of ethanol fermentation, the corn is milled, slurried and cooked to obtain a mash, fermented to obtain a beer, distilled to produce ethanol, and centrifuged to obtain stillage as shown in FIG. 1. Then, once stillage has been produced, the stillage processing method of the present invention can be introduced into the fermentation process at different points in order to obtain certain products, as further detailed below.

Thin stillage can be used in the processing method described in further detail below to generate a stickwater fraction and a ProFat fraction. Thin stillage is obtained by running the centrifuge in the ethanol fermentation process under normal operating conditions.

Alternatively, after the distillation process, the largest solids (for example, greater than 100 μm) can be removed or separated from the whole stillage by use of a centrifuge, filter, membrane, flocculating polymers, dissolved air flotation, or any other suitable separation method to generate a "large solid wet cake" and a thick stillage. For example, thick stillage may be obtained by running the centrifuge in the normal ethanol process at less speed or for less time than is used to generate thin stillage. Additional solids, removal can also be performed on thick stillage to obtain a thin stillage.

By first generating a thick stillage, centrifuge operational reliability is enhanced and more oil and other products can be obtained. DDGS are not materially affected with lower productivity as the ProFat fraction is further separated at high temperature.

Whole stillage can also alternatively be used in the processing method of the present invention and similarly generates a stickwater fraction and a ProFat fraction. In other words heating the stillage at the temperature described herein, whether whole, thick, or thin, results in a stickwater fraction and a ProFat fraction with unique properties. The suspended solids content of the stillage can be varied to tailor the desired amount and composition of products in each fraction.

Also, optionally, if thin stillage is used, additional solids can be added to the stream. The additional solids can be simply added to the thin stillage resulting in a thick stillage. The flexibility of the present invention allows for varying solids concentrations and stickwater can still be obtained.

Figure 2:
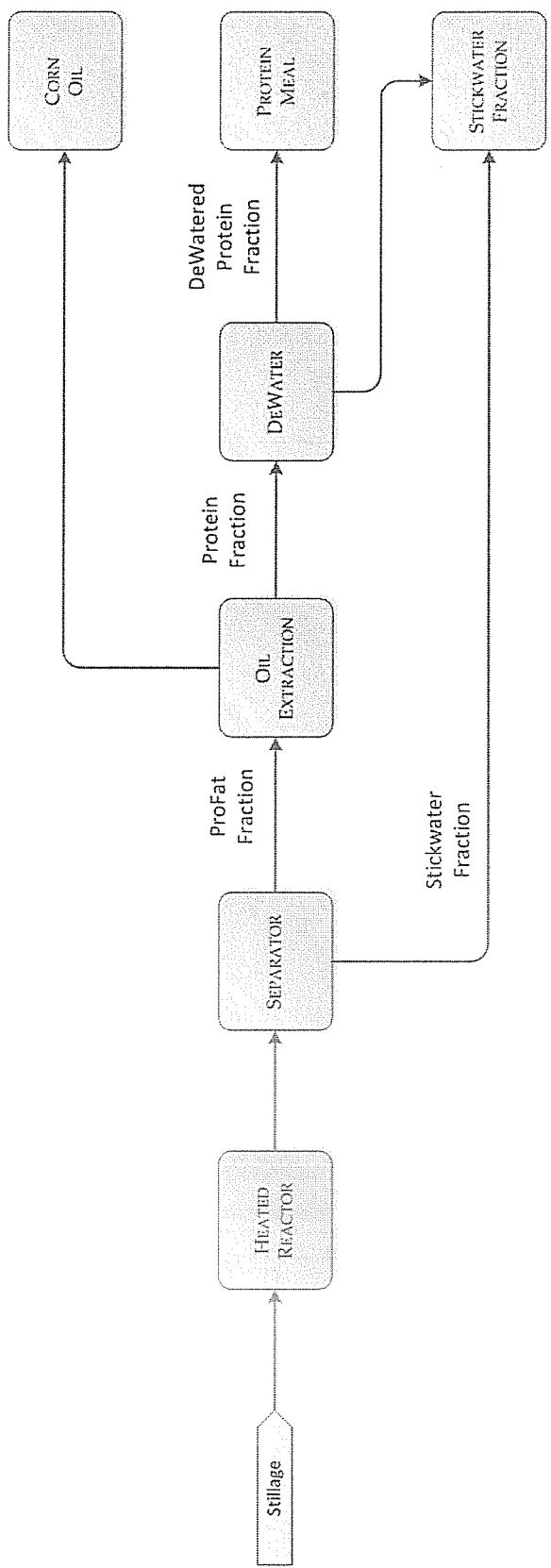
FIG. 2 is a flowchart of the hydrothermal fractionation process of the present invention.

The goal of hydrothermal fractionation is to obtain valuable fractions, reusable water, and improved fermentation media. FIG. 2 shows the main steps of the hydrothermal fractionation method. First, the stillage is heated by a heating mechanism, such as, but not limited to, a heat exchanger or steam injection, to a temperature of 250 degrees F. to 350 degrees F. in a pressurized reactor. More preferably, the stillage is heated to 280 degrees F. to 320 degrees F. The reactor pressure is maintained at or above the saturation pressure of the stillage. The stillage is maintained at that temperature for 3 to 60 minutes. Afterwards, preferably, the stillage is cooled below its atmospheric boiling point, and preferably below 250 degrees F.

The hydrothermal fractionation step essentially "conditions" the stillage to enable facile separation and creates unique product fractions. These altered fractions cannot be obtained in the prior art processes. Unexpectedly, the stillage can separate into a ProFat fraction and a stickwater fraction due to this heating step. In other words, because the heating step causes a physicochemical change to the stillage, the stillage is able to facilely separate into a physicochemical altered ProFat fraction and a physicochemical altered stickwater fraction. The heating step makes the solids in the stillage less hydrophilic and makes it easier for the stickwater phase to separate from the ProFat phase. While further mechanical partitioning processes can also be applied as described below, it is unexpected that merely by heating the stillage at this particular temperature range, the stillage can separate into the ProFat fraction and the stickwater fraction.

In general, the amount of the separation due to the heat itself depends on the degree of solids removal prior to the hydrothermal fractionation step. If stillage with a low suspended solids level is used, the hydrothermal fractionation step readily induces separation. If whole stillage is used, the separation does not happen as readily as with thin stillage and whole stillage can therefore require a further mechanical partitioning or separation step as described below. Thus, in general, the heating step makes it easier to release water from solids in the stillage regardless of the type of stillage used. It should also be understood that the heated stillage can directly be used without separating.

While heating a stillage stream has been performed in the prior art, it has only been done at lower temperatures because of the fear of degrading proteins and sugars and contaminating the stillage with deleterious chemical species. It has been discovered for the first time in the present invention that hydrothermal treatment of stillage at these higher temperatures is not deleterious.

Thus, whether due to the heating step itself, and/or by performing a mechanical separation, the hydrothermally fractionated stillage can be separated or partitioned into two fractions: (1) a ProFat fraction that includes mainly proteins and fats or oils (preferably over 8% total solids w/w and more preferably over 10% total solids w/w), and (2) a stickwater fraction that is mainly water and solubles with a very low amount of suspended solids. The mechanical separation can be achieved with a method such as, but not limited to, gravity (quiescent decantation), centrifugation, decanter centrifugation, dissolved air flotation, or any other suitable method. For example, the separation can be quiescent decantation for 10 to 180 minutes. Alternatively, the stillage can be separated prior to cooling.

There are several separations that can occur once the ProFat and stickwater fractions have been obtained, such as separating ProFat from stickwater; separating protein meal and fat from ProFat; separating oil from stickwater; separating oil from protein meal; separating stickwater from protein meal; simultaneously separating oil, protein meal, and stickwater; and combinations thereof. These separations are further described below.

The ProFat fraction is collected and can be further dewatered or concentrated by centrifugation, dissolved air flotation, evaporation, or any other suitable method. During the method, oil present in the stillage remains primarily with the ProFat fraction and is weight separable. The present invention provides for the oil recovered from the method herein, including corn oil. The de-oiled ProFat resulting from the removal of oil from the ProFat can be recovered as a separate product.

The ProFat fraction has physical properties suitable to mechanical dewatering such that the water separates with traditional methods (belts, decanters). The de-watered ProFat can be recovered as a separate product. The dewatered ProFat can be furthered processed in evaporators or dryers. Water recovered from dewatering the ProFat fraction can either be combined with the first stickwater fraction stream or kept as a separate stream. The dewatered ProFat fraction represents a small portion of the total stillage flow, typically 5%-10%, but has desirable properties, such as a high protein content, that make it valuable. The dewatered ProFat fraction is preferably over 20% solids w/w and more preferably over 25% solids w/w. Alternatively, the ProFat oil recovery and dewatering step can be combined into a single step using a three-phase decanter or other suitable methods.

The stickwater fraction has a very low suspended solids (oil or other solids) content of less than 1%, and the present invention provides for the stickwater recovered from the methods herein. The stickwater fraction can be recycled to the front end of the plant as enhanced backset to form the corn slurry, it can also be sent to the evaporators, or any other suitable point in the ethanol fermentation process. Since the majority of the solids have been removed from the stickwater fraction used as backset, more corn flour can be added to the slurry as compared to when using thin stillage in the slurry, thereby directly increasing the plant's capacity to produce ethanol, DDGS, and corn oil. That portion of the stickwater which is not recycled as backset but is instead forwarded to the evaporators, results in improved evaporator efficiency and operability (less fouling) due to the reduced suspended solids content of stickwater compared to stillage.

Figure 3:
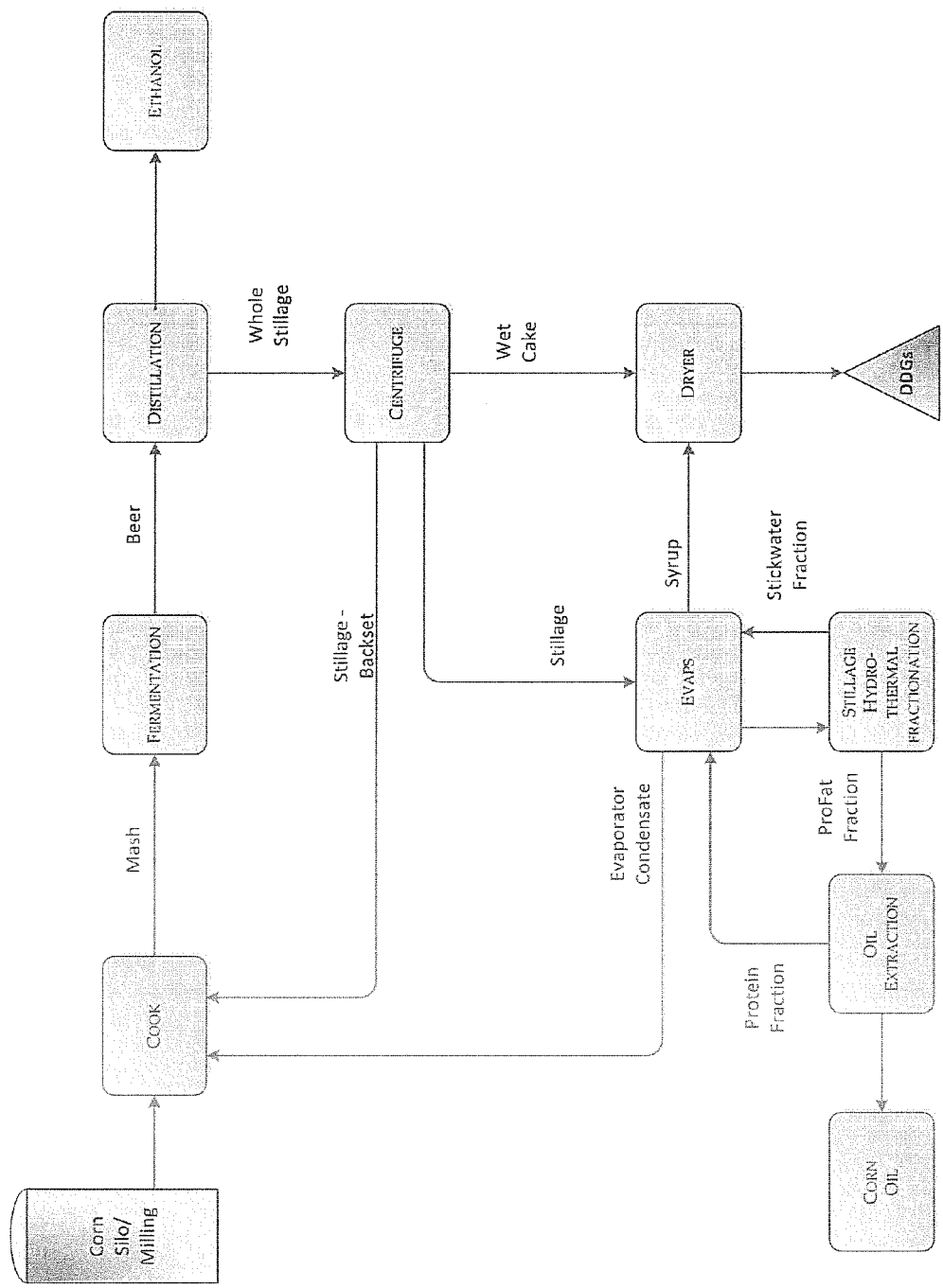
FIG. 3 is a flowchart of the hydrothermal fractionation process of the present invention added to the evaporation step.

There are several places in the main ethanol fermentation process where the stillage processing method as described above can be added. One such option is shown in FIG. 3, wherein the hydrothermal fractionation is performed on evaporated stillage concentrate. The stickwater fraction can be returned to the front end of the process or some or all of the stickwater fraction can be further processed as described below. Oil (such as corn oil) is recovered from the ProFat fraction, and the rest of the ProFat fraction is sent to a dryer to recover syrup solubles to add to the DDG.

Therefore, the present invention provides for a method of performing ethanol fermentation, including the steps of conditioning concentrated stillage to enable facile separation and create unique product fractions by heating the stillage to a temperature of 250 degrees F. to 350 degrees F., separating the stillage into a ProFat fraction and a stickwater fraction, and recovering oil from the ProFat fraction.

The method can also further include before the concentrating step, the steps of cooking, fermenting, and distilling corn and obtaining ethanol, separating whole stillage into stillage and wet cake. The method can further include, after the partitioning step, the steps of recovering oil, drying the ProFat and obtaining dried distillers grains, obtaining a stickwater fraction, and recycling the stickwater fraction.

Figure 4:
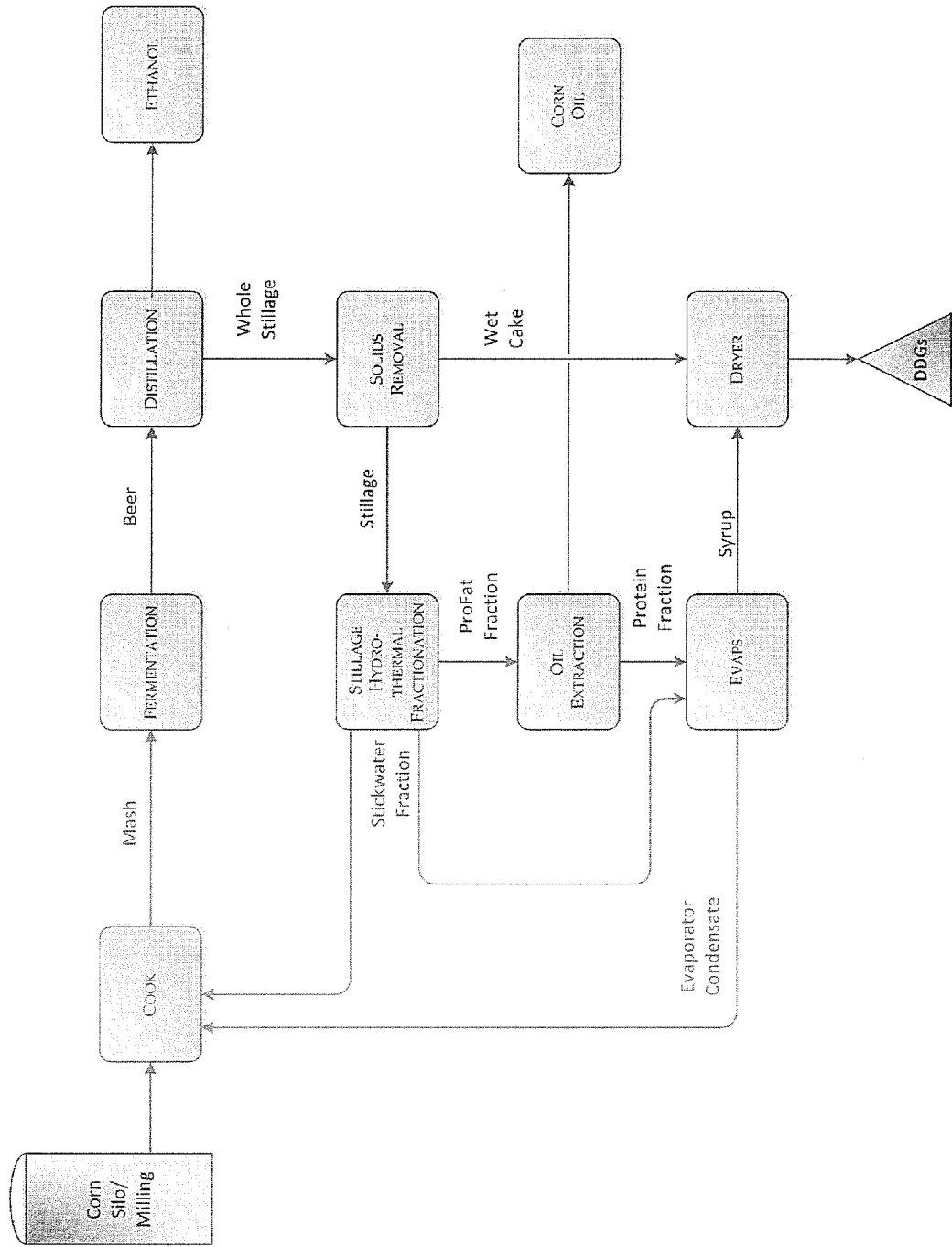
FIG. 4 is a flowchart of the hydrothermal fractionation process of the present invention added after separating whole stillage into stillage and wet cake.

Another processing option is shown in FIG. 4. Large solids can be removed from the stillage, if desired. The stillage is hydrothermally fractionated then separated into a ProFat fraction and a stickwater fraction. Oil (such as corn oil) can be extracted from the ProFat fraction and the oil and protein fraction can be recovered. Stickwater can be sent to the cook step at the front end of the process as enhanced backset. Some or all of the stickwater and protein fractions can be sent to the evaporators, and separated into the evaporator condensate that is sent back to the cook step, and the concentrated, protein fraction that is sent to the dryer as syrup to add to and recover DDGS.

Therefore, the present invention also provides for a method of performing ethanol fermentation, including the steps of separating whole stillage into stillage and wet cake, performing the method of hydrothermal fractionation as described above, recovering a stickwater fraction, a protein fraction and oil, and recycling some or all of the stickwater to the cook step as enhanced backset.

Also, before the whole stillage separating step, the method can include the steps of cooking, fermenting, and distilling corn and obtaining ethanol, and, after recovering the stickwater fraction and the protein fraction and oil, the method can further include the steps of evaporating the stickwater fraction and the protein fraction, recovering evaporator condensate and recycling to the cooking step; and recovering concentrated protein fraction and drying the concentrated protein fraction and obtaining dried distillers grains.

Figure 5:
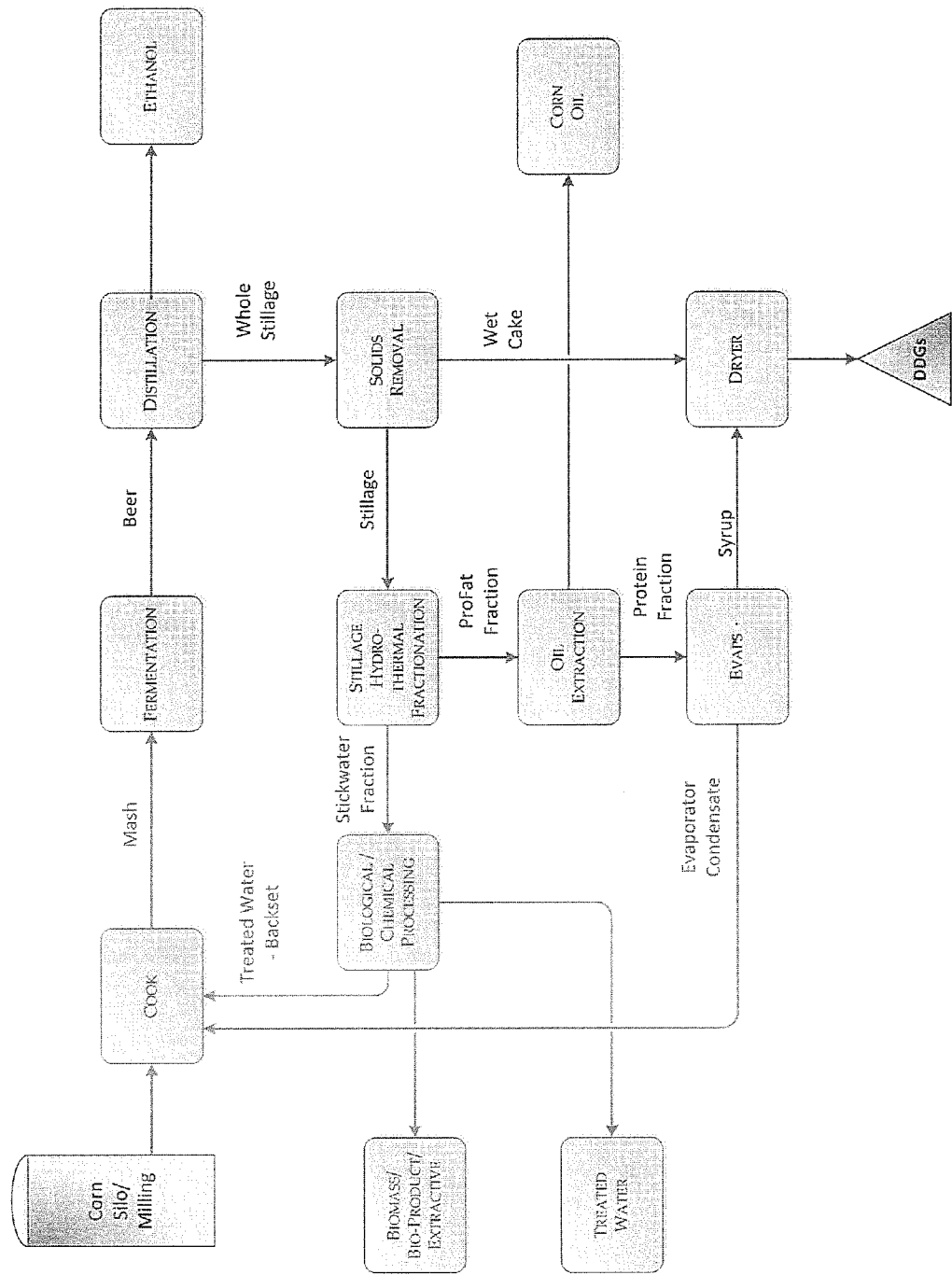
FIG. 5 is a flowchart of the hydrothermal fractionation process of the present invention added after separating whole stillage into stillage and wet cake and including biological/chemical processing of stickwater.

The process shown in FIG. 4 can be further altered so that the stickwater fraction produced by hydrothermal fractionation is sent for further biological or chemical processing as shown in FIG. 5. The stickwater fraction can be treated biologically to further remove fermentation inhibitors. Metabolites that are fermentation inhibitors are still present in the stickwater fraction after separation, but without the suspended solids, they can more easily be removed with standard industrial processes such as anaerobic digestion.

Alternatively, algae, fungi, or any other suitable microorganisms can be added to the stickwater fraction and the stickwater fraction acts as an improved growth media. Components in the stickwater, including trace minerals, proteins, and carbohydrates can be used by various micro-organisms. Yeast metabolites, such as glycerol and organic acids, can be used as a carbon source by GMO (genetically modified organism) and non-GMO micro-organisms. These micro-organisms can produce biomass, ethanol or other higher value biofuels or bio-based chemicals. For example, a modified *E. coli* or yeast can metabolize glycerol to ethanol. After the biological treatment, the stickwater fraction can be recycled or sold.

The low solids stickwater can be further processed in order to selectively isolate components. The stickwater fraction can be concentrated by evaporation or membrane separation. Membranes can be used to perform ultrafiltration and/or nanofiltration of the stickwater fraction to result in demineralized water stream that is essentially free of dissolved solids and organic compounds larger than membrane pores. Multiple membranes can be used in series. A reverse osmosis (RO) membrane can also be used after the aforementioned filtration steps. Any components isolated by the membranes can be recovered for additional use, such as, but not limited to, lactic acid and glycerol. Additionally, the stickwater can also be chemically treated by addition of acids, bases or other agents to precipitate and recover minerals and salts and/or by addition of solvents to extract metabolites, organic components or plant extractives.

After the biological or chemical processing steps described above, biomass, bio-products, metabolites, and/or extracts can be recovered along with treated water. The treated stickwater can be sold or recycled to the cook step for further use.

Figure 6:
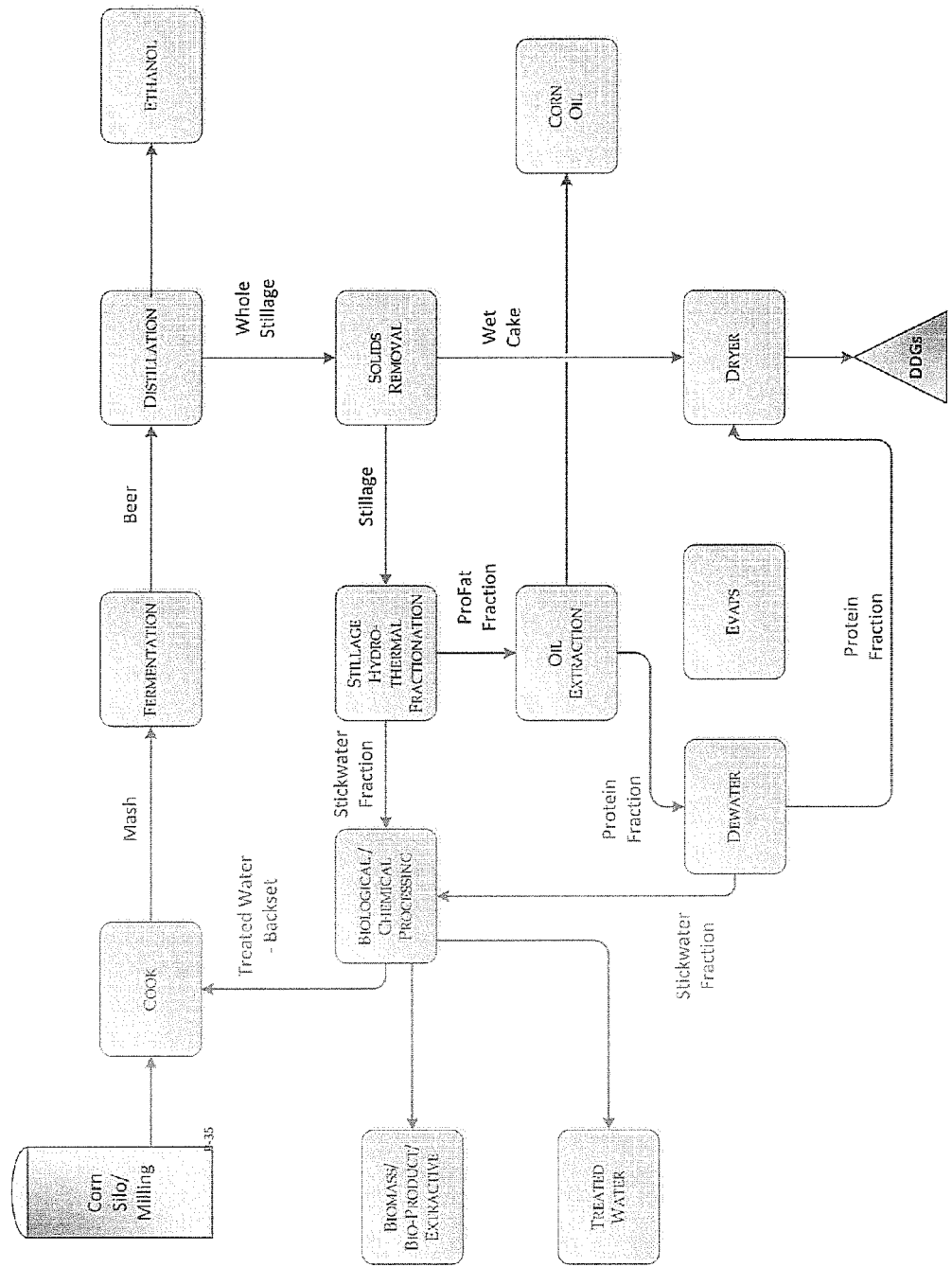
FIG. 6 is a flowchart of the hydrothermal fractionation process of the present invention added after separating whole stillage into stillage and wet cake and including dewatering of the ProFat fraction and adding the dewatered ProFat to the wet cake.

A further option is shown in FIG. 6, also based on the placement of the hydrothermal fractionation in FIG. 5. In this process, once the protein fraction has been recovered, the protein fraction is dewatered, producing an additional stickwater stream that is sent to the biological or chemical processing step, and a dewatered protein fraction stream that is combined with the wet cake and sent to the dryer to produce dried distillers grains. This process totally eliminates the need for evaporators and reduces cost.

Figure 7:
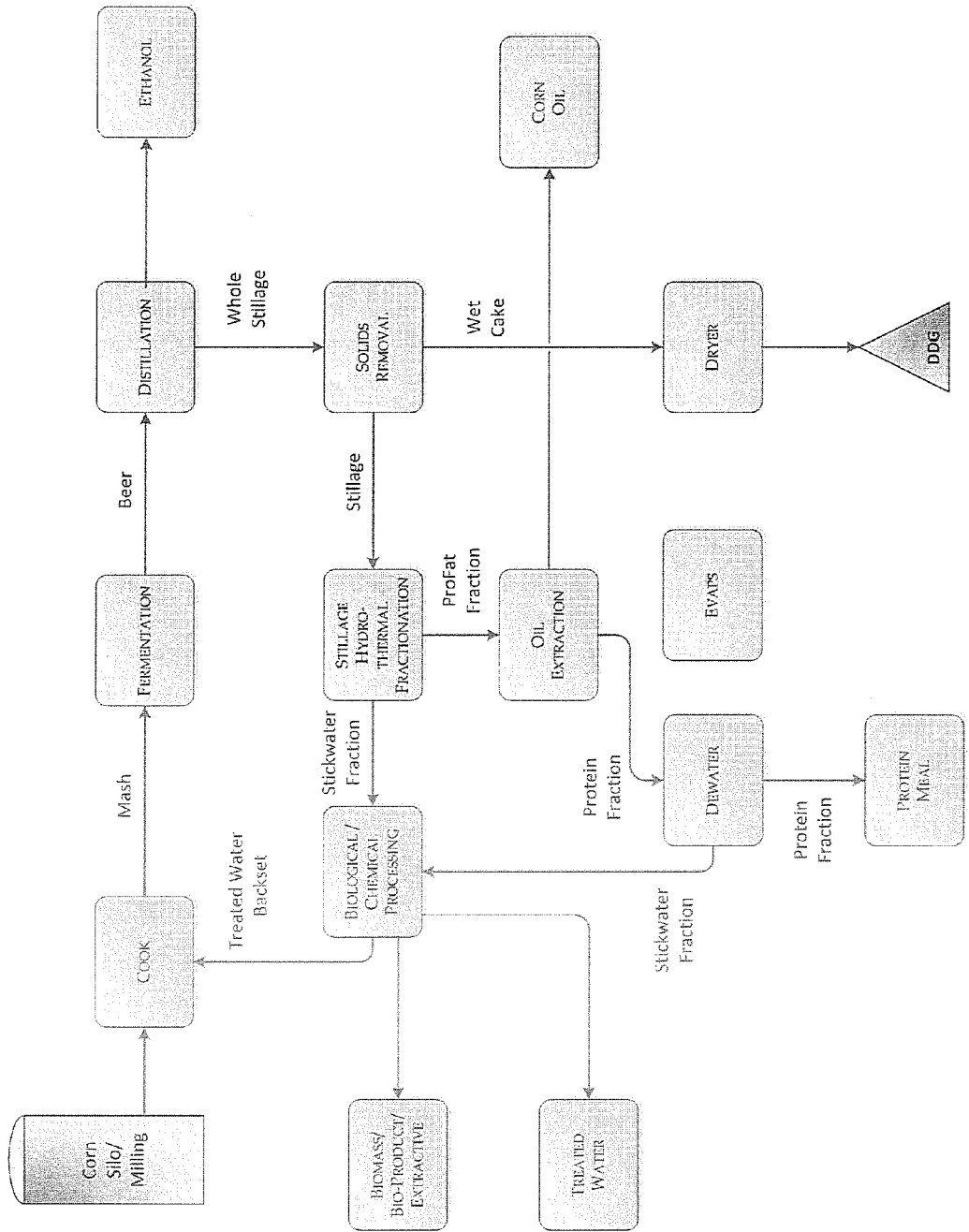
FIG. 7 is a flowchart of the hydrothermal fractionation process of the present invention added after separating whole stillage into stillage and wet cake and including dewatering of the ProFat fraction to produce a high protein meal.

The process in FIG. 6 can be further altered as shown in FIG. 7. The dewatered protein fraction can be recovered and dried as a separate product (protein meal).

There are several advantages to the processes of the present invention described herein over prior art processes. First, there are components in the stillage that are fermentation enhancers. For example, the proteins from corn and yeast present in the stillage can potentially supply a source of beneficial amino acids if properly treated prior to recycle to fermentation. Other insoluble components in the stillage can be fermentation enhancers when solubilized by the present invention. With the stickwater of the present invention, fermentation rates and final titers can be increased.

Second, the present invention allows for the elimination of evaporators. Evaporator condensate that was previously used as make-up water in the cook process can be replaced with additional stickwater. Also, evaporating stillage is energy intensive in prior art processes. Even with the use of multi-effect evaporators, the energy used in evaporation of thin stillage can be as high as 3,000 BTU/gallon of ethanol produced, approximately 10% of all thermal energy used by the plant. Although ethanol plants are highly energy efficient and the energy used in evaporation is recycled to other unit operations, usage minimization or elimination of the evaporators will allow the energy currently utilized for evaporation to be repurposed, such as a Heat Recovery Steam Generator.

Third, the recycled stillage can be detrimental to fermentation in prior art processes. The yeast metabolites produced during fermentation and present in the stillage can act as fermentation inhibitors. Examples are glycerol, lactic acid, and acetic acid, among others. The low suspended solids in the stickwater from the present invention allows for more efficient removal of these inhibitors by application of biological treatment, filtration, or other methods.

Fourth, the suspended solids in the stillage are not fermentable and reduce the amount of new corn flour that can be added to the slurry, as corn ethanol plants typically run at a target total solids through fermentation to maximize the ethanol produced per bushel of corn processed. By reducing detrimental solids in the backset, hydrothermal fractionation of the present invention can increase ethanol plant efficiency and throughput.

Fifth, stillage, if properly treated is an improved growth media for the production of biomass and bio-products. Thus, one additional use of the stickwater fraction is fermentation media for algae, fungi, and other useful microorganisms. The treated stickwater can be sold as media basestock or aqueous feed along with the other bio-products produced instead of or in addition to being recycled back to fermentation to produce more ethanol.

Sixth, the stillage contains a large portion of corn oil. Corn oil is up to four times more valuable if extracted than if left in the stillage. However, the corn oil is emulsified in the stillage and does not lend itself to extraction easily. Also, it is impractical and expensive to process the entire flow of stillage to extract the oil. With the process of the present invention, the oil can be extracted with a gravity based separation apparatus, Practicing the present invention, between 0.8-1.3 lb corn oil can be recovered per bushel of corn processed into the plant as compared to processes of the prior art where typical yields are 0.4-0.6 lb corn oil per bushel.

Therefore, in summary, the present invention provides for a method of performing ethanol fermentation, including the steps of separating whole stillage into stillage and wet cake, performing the method of hydrothermal fractionation described above, recovering a first stickwater fraction, recovering a ProFat fraction, extracting oil from the ProFat fraction, recovering corn oil and protein fraction, dewatering the protein fraction, obtaining a dewatered protein fraction and a second stickwater fraction, and adding the second stickwater fraction to the first stickwater fraction, further biologically or chemically processing the first and second stickwater fractions and using the first and second stickwater fraction as growth media. The method can also include, before separating the whole stillage into stillage and wet cake, the steps of cooking, fermenting, and distilling corn and obtaining ethanol. The method can include after the further processing step, the steps of recycling some or all of the stickwater to the cook step as enhanced backset, recovering biomass, bio-products, extracts, metabolites, and treated water from the growth media and recycling the treated water. The method can further include drying the protein fraction, or if the dewatering step is utilized, the dewatered protein fraction and recovering a high protein meal. Optionally, the protein fraction, or if the dewatering step is utilized, the dewatered protein fraction can be added to the wet cake, and dried, recovering dried distillers grains.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

ANALYTICAL METHODS COMMON TO MULTIPLE EXAMPLES

The following analytical methods, shown in TABLE 1, established by AOAC International, were used throughout multiple examples. Other methods are described within specific examples.

TABLE 1

| Analysis | AOAC Method # |
| --- | --- |
| Dry Weight or Total Solids (w/w) | 934.01 (24 h, 105 deg C. Method) |
| Total Suspended Solids | 934.01 applied to the wet cake of a sample filtered through 2.2 μm filter media. |
| Amino Acid analysis: | 994.12 |
| Neutral Fiber | 962.09E (neutral detergent fiber) |
| Crude Protein | 970.09 (Kjehldahl method) |
| Crude Fat/Oil | 920.39C Ether extraction method) |

Example 1

Analysis and Comparison of Treatment of Thin Stillage by Invention

Procedures

For the present EXAMPLE 1, thin stillage obtained from a commercial ethanol plant was continuously pumped through a series of Plate and Frame Heat Exchangers (PHEs) into a stirred reactor. The PHEs heated the stillage to 285 F. The reactor's pressure was maintained at the saturation pressure of the stillage. The reactor had a mean residence time of 48 minutes. The conditioned stillage was continuously withdrawn from the reactor and cooled to 185 F, then held in a quiescent decantation tank with a mean residence time of 40 minutes. The stickwater fraction and ProFat fraction were continuously removed from the decantation tank and collected. The volume ratio of Stickwater to ProFat was 1:1.

Methods of Analysis

The AOAC analytical methods listed above were used in this example.

Results and Discussion

TABLE 2 shows a comparison of thin stillage, stickwater and ProFat fractions.

TABLE 2

|  | Thin Stillage | ProFat | Stickwater |
| --- | --- | --- | --- |
| Total Solids (w/w) | 8.02 | 8.7 | 6.84 |
| Fat (w/w) | 1.12 | 2.30 | 0.09 |
| Protein (w/w) | 0.99 | 1.18 | 0.65 |

The thin stillage was partitioned into two distinct fractions; a ProFat fraction and a stickwater Fraction. The ProFat fraction had higher total solids, fat and protein as compared to both thin stillage (8%, 105%, and 19% higher respectively) and stickwater (27%, 2456%, and 82% higher respectively).

Example 2

Analysis and Comparison of Low G Separation of Untreated Thin Stillage and Thin Stillage Treated by Invention Procedures For the present EXAMPLE 2, untreated thin stillage was obtained from a commercial ethanol plant. The untreated thin stillage was collected at approximately 175 F. Treated stillage was prepared by heating collected thin stillage to 280 F in a stirred batch reactor, held for 40 minutes, and then cooled to approximately 175 F. One liter containers of treated and untreated stillage at approximately 175 F were centrifuged at 400×G for 30 seconds. The samples were then divided into a top fraction, middle fraction and bottom fraction, each representing ⅓ of the original sample.

Methods of Analysis

The AOAC analytical methods listed above were used in this example

Results and Discussion

Figure 8:
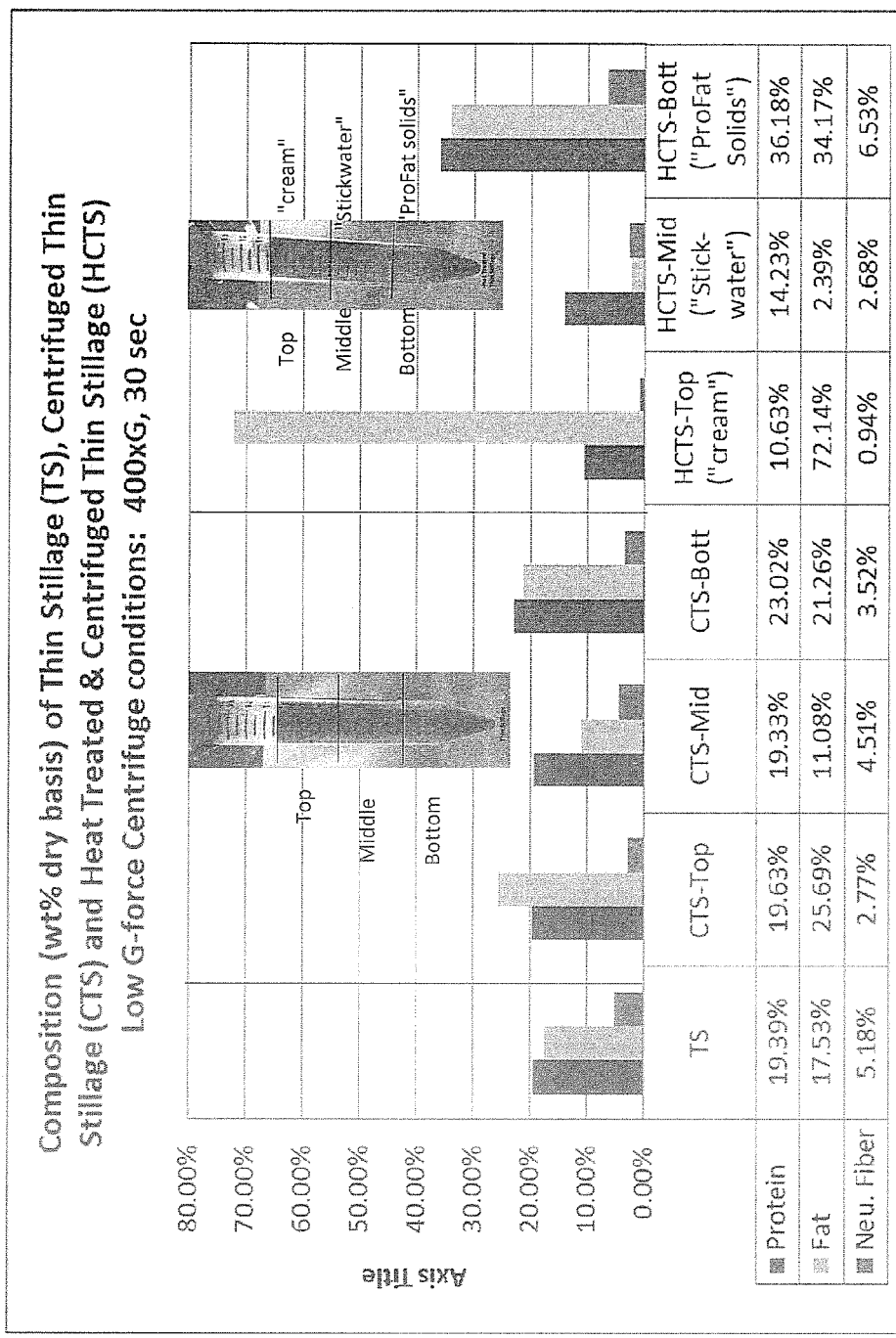
FIG. 8 is a graph showing the composition of untreated thin stillage and hydrothermally fractionated thin stillage after low G-force separation.

FIG. 8 shows a compositional comparison of the three fractions from the treated and untreated thin stillage centrifuged in 1 liter containers. The photos are of the same samples prepared in 15 mL test tubes which provide a clearer visual depiction (than 1 liter bottles) of the formation of sediment in the ProFat fraction of the treated samples under short duration, low g-force conditions. Sediment was not observed in the untreated sample under low g-force conditions, a further indicator of the facile separation induced by the present invention. The data in FIG. 8 clearly shows that there is no significant partitioning of components top-to-bottom in the untreated stillage sample (CTS) while strong partitioning of components occurs in the heat treated sample (HCTS) even under low g-force conditions. In particular, the ProFat fraction is substantially enhanced in fat and protein content relative to thin stillage and the top "cream" portion of the treated sample is likewise enhanced in fat content.

Example 3

Fractionation of Profat to Co-Products and Comparison to Thin Stillage and DDGS Procedures A ProFat fraction produced by the method of EXAMPLE 1, was further fractionated by a tricanter into a second stickwater fraction, an oil fraction and a de-watered de-oiled protein fraction. This final protein fraction was analyzed for dry weight total solids, protein, amino acids, and oil.

The ProFat fraction was collected and pumped at a rate of 3 gpm through an Andritz Decanter Model D3L operating at 3000 G. Oil was collected from the skimmer, the second stickwater fraction was collected as the centrate and the de-oiled de-watered protein fraction was collected as the wet cake.

Untreated thin stillage was also collected and pumped at the same rate through the same decanter at the same settings.

The wet material was then dried in a 105° C. oven overnight and then analyzed for dry weight, protein, oil and amino acids.

Methods of Analysis

The AOAC analytical methods listed above were used in this example.

Results and Discussion

The dewatered wet cake of the ProFat fraction is compared to the wet cake of dewatered thin stillage in TABLE 3. The ProFat fraction easily dewatered in the decanter whereas the thin stillage showed virtually no dewatering. This experiment demonstrated the hydrophobic nature and superior dewatering of the ProFat solids processed in accordance with this invention.

TABLE 3

Comparison of Wet Cake from Decanter Dewatering

|  | Untreated Thin Stillage | | ProFat | |
| --- | --- | --- | --- | --- |
|  | Decanter Feed | Decanter Wet Cake | Decanter Feed | Decanter Wet Cake |
| Total Solids (% w/w) | 4.9 | 4.9 | 9.1 | 24.2 |

In TABLE 4, the weight, protein, fat and neutral fiber analyses for two preparations of the protein fraction (i.e. de-oiled de-watered ProFat) of the present invention are compared to published data for DDGS. The unique Protein fraction produced by the present invention has more protein, significantly more fat and significantly less neutral fiber than DDGS.

TABLE 4

Comparison of Protein Fraction to DDGS

|  | Protein Fraction (de-oiled, de-watered ProFat) | | |
| --- | --- | --- | --- |
|  | Sample A | Sample B | DDGS[b] |
| Protein[a] | 43.4 | 44.1 | 31.2 |
| Fat[a] | 35.7 | 38.7 | 11.5 |
| Neutral Fiber[a] | 1.0 | 0.9 | 42.3 |
| Other by difference | 19.9 | 16.3 | 15.0 |

[a]Expressed as a % of the dry wt.
[b]Average values from Fastinger and Mahan, (J. Anim. Sci. 84: 1722-1728, 2006) and Stein et al. (J. Anim. Sci. 84: 853-860, 2006) as presented in A. A. Pahm's Ph. D thesis U. of ILL, p. 66 Table 2.1, 2008.

This example illustrates the utility of the invention. A corn ethanol plant can recover a new, high value co-product that is significantly different than the current DOGS co-product. Again, due to the facile separation resulting by heating; proteins, fats, and fibers are obtainable in amounts that would otherwise not be possible to obtain by prior art processes.

Example 4

Ethanol Fermentation Improved by Stickwater

Dry-grind corn ethanol plants recycle their thin stillage to the front end of the plant to be used as make up water in the cook and fermentation processes. In this example, both thin stillage obtained from a commercial ethanol plant and stickwater prepared thereof were used as the basis for a fermentation medium to which anhydrous glucose was added as a carbon source. No other nutrients were added, thereby showing that the stickwater can be a superior media compared to thin stillage.

Procedures

Stickwater was prepared and collected as in EXAMPLE 1.

Culture and Fermentation

The batch fermentations were started with an initial culture of a commercial ethanol producing *Saccharomyces cerevisiae* (Ethanol Red®, obtained from Fermentis div. of Lesaffre). Two batches of stickwater were produced from commercial thin stillage based on the methods described above, and the resultant stickwater from each batch were then compared to an original sample of thin stillage for ethanol fermentation performance. To a 1 liter sample of thin stillage or stickwater, approximately 200 grams of anhydrous glucose was added as the carbon source and allowed to dissolve. The resultant glucose/sample was added to an autoclaved 1.5 liter stirred reactor (Pyrex® Pro-Culture Spinner Flask (1.5 L); Corning, Corning, N.Y.) and the temperature of the fermentor was equilibrated to 82° F. prior to inoculation.

Inoculum

The inoculum was prepared in a 250 ml sterile Erlenmeyer flask by addition of 1 gram of lyophilized yeast into 100 ml of filter sterilized 2% (w/w) malt extract broth and was incubated at 82° F. for 30 minutes before use. From the inoculum, 5 ml was used to start the fermentations.

Batch Fermentation

An initial sample was taken prior to inoculation and frozen. The fermentation was done at 82 F with 110 rpm agitation. Fermentation vent locks were fitted to the fermenters at 1 hour after inoculation, to prevent oxygen from entering the vessel. At various time points, samples were removed and frozen prior to analysis via HPLC. After 48 hours the fermentations were stopped.

Methods of Analysis

HPLC analysis for sugars and organic acids is based on NREL method LAP 015. Analysis was performed on a Phenomenex Rezex ROA-Organic acid column at 55° C. using 0.005 N sulfuric acid as the eluent and flow rate set at 0.6 ml/min. The detection was via a UV/Vis detector set at 190 nm and CAD (Charged Aerosol Detector). Samples were unthawed, diluted, filtered through a 0.2 micron nylon filter. The injection volume was 20 µl and the samples were compared against standards Results and Discussion TABLE 5 demonstrates that stickwater provides a superior fermentation medium for ethanol production as compared to thin stillage. Stickwater improved both the rate of ethanol production and yield of ethanol on dextrose versus untreated thin stillage. The theoretical yield of ethanol on dextrose is 51.14 wt % [calculated as 2 mols ethanol*46.068 g/mol)/(1 mol dextrose*180.16 g/mol)=0.5114]. A yield in excess of 51.14 wt % for both of the treated samples in this example indicates that the stickwater of the present invention provides nutrient value not supplied by untreated thin stillage, thus enhancing the value of stickwater as backset. Additionally this example shows that 100% of the produced stickwater may be recycled as backset without deleterious impact on fermentation performance.

TABLE 5

Ethanol Fermentation results with Stickwater versus Untreated Thin Stillage

| Fermentation Metric | Sample A | Sample B | Average of Treated Samples | Untreated Thin Stillage (Control) |
|---|---|---|---|---|
| Ethanol Production Rate (g ethanol/l/hr) | 1.97 | 1.95 | 1.96 | 1.67 |
| Ethanol yield on dextrose (wt %) | 51.7% | 52.9% | 52.3% | 43.5% |

Example 5

Analysis and Comparison of Stickwater and Thin Stillage as Fermentation Media for Other Microorganisms In this example, an oleaginous yeast, *Lipomyces starkeyi*, was chosen as the model microorganism for fermentation. *L. starkeyi* was chosen due to its ability to grow on a variety of carbon sources and nitrogen sources. Stickwater prepared by the present invention is compared to thin stillage.

Procedures

Stickwater was prepared and collected as in EXAMPLE 1.

Yeast and Fermentation

Both thin stillage and stickwater were sterile filtered through 0.2 micron cellulose acetate membrane prior to inoculation. *Lipomyces starkeyi* Y-11557 was obtained as ampoules of lyophilized solid from the USDA NRRL culture collection (NRRL, Lab Peoria, Ill.). The inoculum was prepared by adding the full ampoule of lyophilized yeast into a 250 mL sterile shake flask containing 100 mL of filter sterilized 2% malt extract medium and then grown for 24 hours at 25° C. and 110 rpm agitation to produce cells in logarithmic growth phase. The fermentations were performed in sterile 1.5 liter stirred vessels (Pyrex® Pro-Culture Spinner Flask (1.5 L); Corning, Corning, N.Y.) charged with 1 liter of fermentation medium, air flow of 0.95 SLPM, agitation rate of 110 rpm and 80-82° F. A 5 ml inoculum sample was used to start the fermentation and growth was then monitored for 48 hours.

Methods of Analysis

Samples were removed during the course of fermentation and analyzed for microscopic cell count and dry weight (AOAC method). Microscopic cell counts were performed with an improved Neubauer Counting Chamber using serial dilutions in sterile water as the diluent.

Results and Discussion

In the present example, the stickwater and thin stillage samples were sterile filtered to prevent the potential contamination of the *L. starkeyi* fermentation batches by foreign micro-organisms. Filtration effectively removed all suspended solids greater than 0.2 µm. Hence the impact of soluble components and any residual ultra-fine suspended solids in the stickwater and thin stillage media is highlighted by this example. TABLE 6 shows the final (48 hr) dry weights of the *Lipomyces* grown on stickwater versus clarified thin stillage. The total dry weight of the biomass grown on stickwater was 28.6% higher than that grown on clarified thin stillage.

Figure 9:
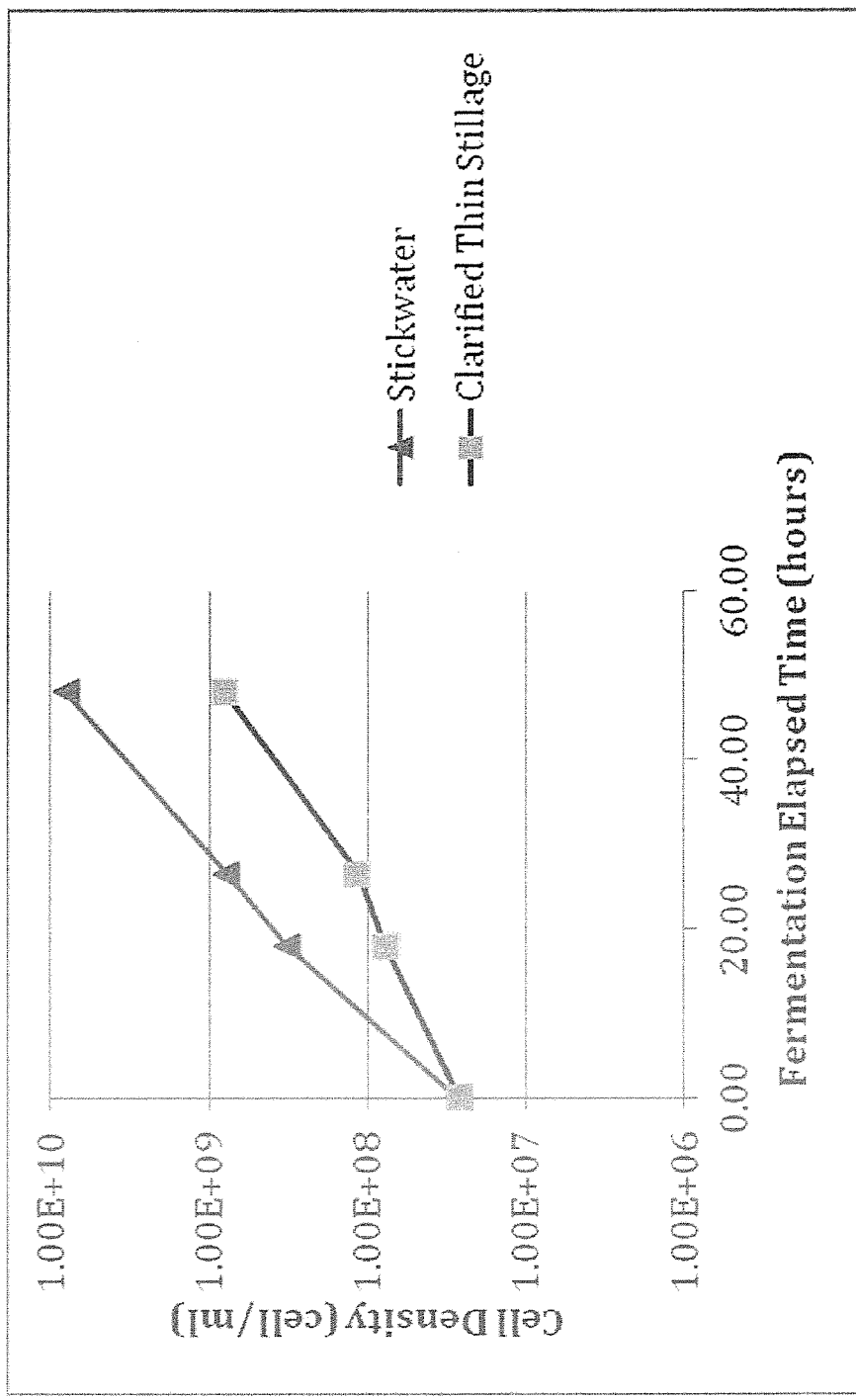
FIG. 9 is a semi-log plot of cell counts versus time for growth of *Lipomyces starkeyi* on stickwater vs. thin stillage.

FIG. 9 shows the difference between *Lipomyces* grown on stickwater versus clarified thin stillage in total cell count. The graph shows that growth on filtered stickwater is much more rapid than growth on filtered thin stillage indicating that the soluble components and any residual ultra-fine suspended solids contained in stickwater provide an advantaged growth medium. Furthermore, this example shows that even fine filtration of thin stillage is not sufficient to provide the unique growth media properties provided by stickwater.

An ethanol plant could diversify its product lines by adding biomass fermentation utilizing stickwater as a medium. An economic advantage is anticipated due to the enhanced growth performance of stickwater versus thin stillage.

TABLE 6

Dry Weight comparison of *Lypomyces Starkeyi*

|  | Stickwater | Clarified Thin Stillage |
|---|---|---|
| g/l Dry Weight | 3.01 | 2.34 |

Example 6

Treatment of Thin Stillage by Invention at Various Times and Temperatures

Procedures

For the present EXAMPLE 6, thin stillage was obtained from a commercial ethanol plant and heated to various times and temperatures within the parameters of the invention, cooled and allowed to separate by means of quiescent decantation. The thin stillage was heated by flow through a PHE and then held in a batch pressurized reactor. Partitioning by quiescent decantation was performed and the stickwater and high solids ProFat fractions were collected and analyzed by a rapid dry weight method.

Methods of Analysis

In this example dry weight analysis was performed with a Mettler Toledo MJ33 moisture balance according to manufacturer's instruction. Briefly, 5-10 g of sample was added to the scale, the scale was tared and the sample was heated to 120° C. and held until a 0.01 g weight difference is measured per minute. This method is rapid compared to the AOAC dry weight method;

Results and Discussion

A clear and facile separation of the stickwater and ProFat (high solids) phases by quiescent decantation was visually observed for all samples treated in the range of 250-325 F and 10-60 minutes residence time. By comparison, untreated thin stillage shows no phase separation by quiescent decantation. TABLE 7 shows a comparison of the total solids of the stickwater fraction over the range of treatment times and temperatures tested. The thin stillage from which these stickwater samples were derived had a total solids concentration of 8.08 wt %. It is observed in TABLE 7 that higher temperatures allow for similar partitioning of solids to occur at lower residence times.

TABLE 7

| | Stickwater Total Solids (% w/w) at Treatment Temperature | | | | |
|---|---|---|---|---|---|
| Residence Time | 250° F. | 280° F. | 300° F. | 315° F. | 325° F. |
| 10 min. | | | | | 6.23 |
| 20 min. | | 7.27 | 6.18 | 6.25 | |
| 40 min | 7.34 | 6.34 | 5.73 | | |
| 60 min | 6.57 | | | | |

Figure 10:
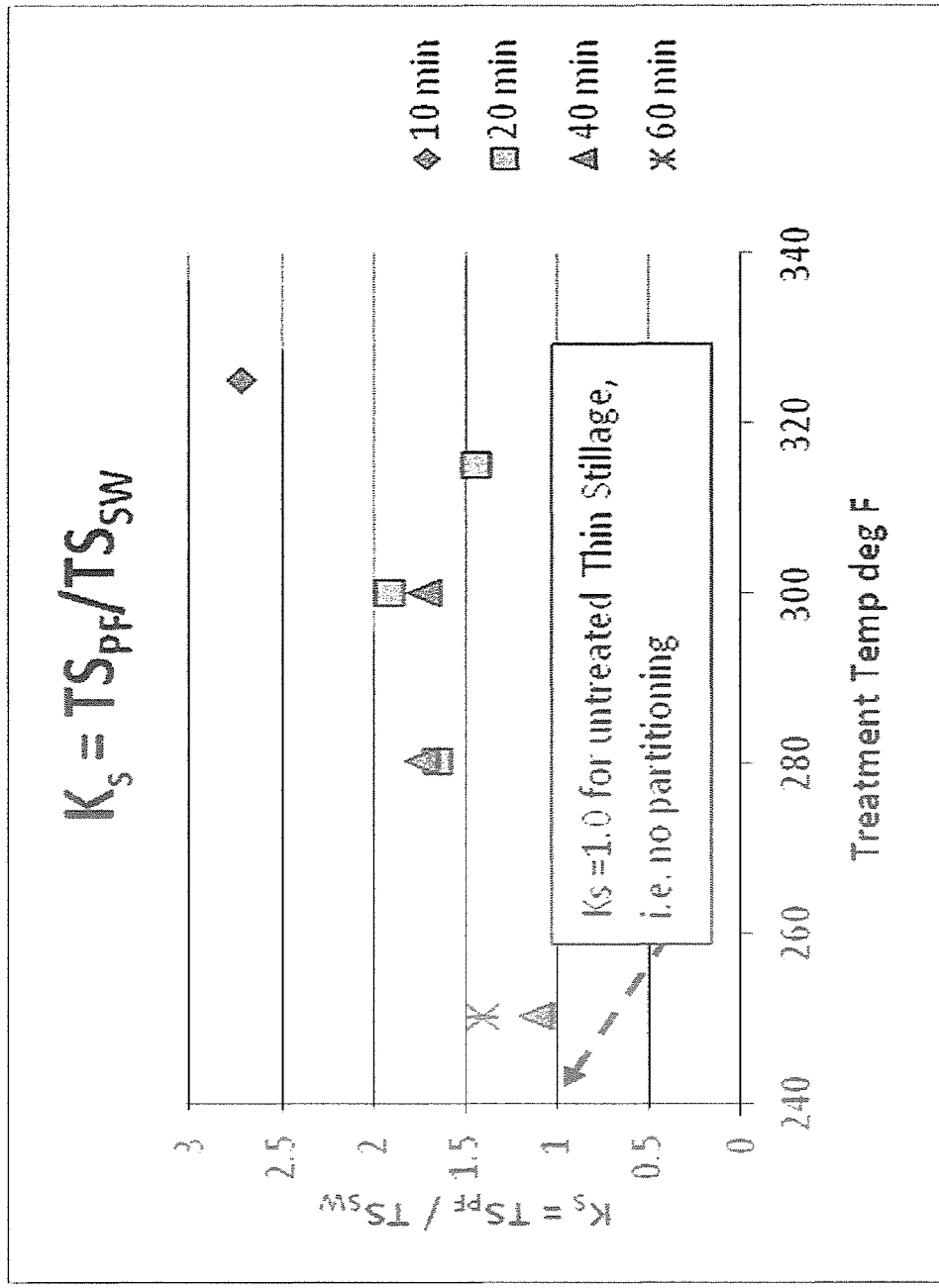
FIG. 10 is a graph of the solids partitioning factor, $K_s$, for thin stillage treated by hydrothermal fractionation over a range of time and temperatures. $K_s = TS_{PF}/TS_{SW}$ = wt % total solids in ProFat fraction/wt % total solids in Stickwater fraction.

Data for the total solids concentration of the ProFat fraction (not shown) and the average stickwater solids at each temperature (TABLE 7) were used to calculate a solids partitioning factor, $K_s$, as shown in FIG. 10. Untreated thin stillage does not partition (phase separate), and hence $K_s$ in the sense of a true biphasic system is not measurable; however, for comparison purposes the $K_s$ of untreated thin stillage in is taken to be 1.0 for a monophasic system. FIG. 10 shows that the degree of solids partitioning and hence the composition of the unique product fractions can be tailored based on the time and temperature selected for hydrothermal fractionation.

Example 7

Fermentation of Thick Stillage

In this example, the flexibility of the present invention to produce advantageous stickwater from stillage of varying solids concentrations, i.e. thin stillage, thick stillage and whole stillage, is demonstrated. The advantage of whole stillage or thick stillage, prepared by filtration for example, is that they offer higher recoverable oil concentrations than thin stillage (reference TABLE 8 below.

Procedures

Whole stillage and thin stillage were obtained from a commercial ethanol plant. To produce stillage having a suspended solids concentration between that of whole and thin, whole stillage was filtered through a series nylon filter bags of decreasing pore size (1000, 600, 400, 100 microns). Filtrate from the 100 micron filter was taken as "thick stillage". Samples of thin stillage, whole stillage and thick stillage were analyzed for total solids, suspended solids and % oil. The resultant material was thermally conditioned at 270 F for 40 minutes, and then separated to produce a stickwater fraction. The stickwater fraction was used as fermentation medium for ethanol production, as previously described in EXAMPLE 4.

Results and Discussion

Figure 11:
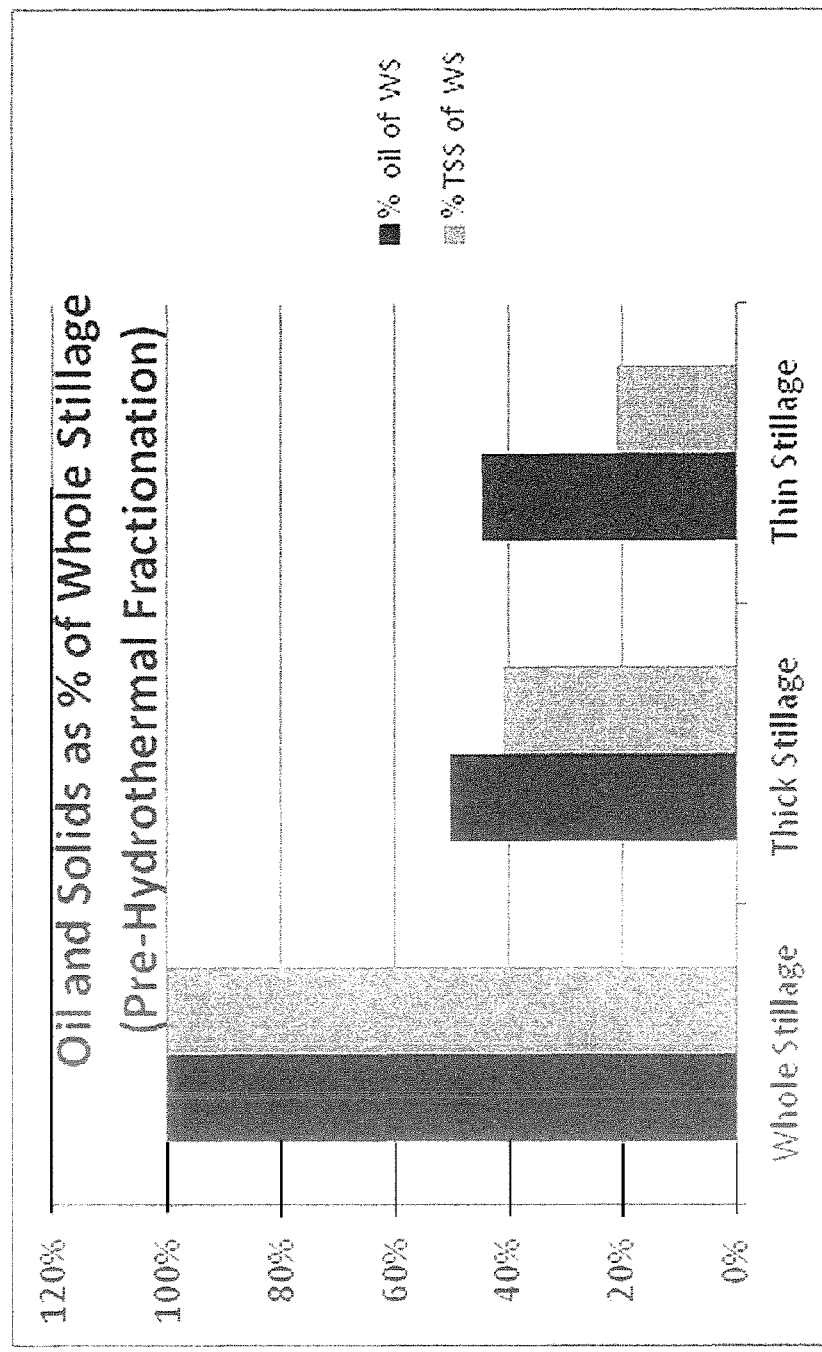
FIG. 11 is a graph of Oil and Total Suspended Solids as percentages of whole stillage for whole, thick and thin stillage samples prior to hydrothermal fractionation.

TABLE 8 and FIG. 11 give oil and solids levels prior to hydrothermal treatment and illustrate that a significant percentage of the oil is associated with the suspended solids. Thus, a process which can flexibly treat high and low solids stillage streams will be advantageous. TABLE 8 shows that stickwater prepared by the present invention from any of the stillage concentrations can be used as fermentation media with no loss of performance. The ability to produce stickwater from thin, thick or whole stillage is an unexpected result of the present invention and can provide the ethanol producer with greater oil yield, advantageous fermentation yields and process flexibility.

TABLE 8

Oil and Solids prior to Hydrothermal Fractionation

| | Whole Stillage | Thick Stillage | Thin Stillage |
|---|---|---|---|
| Total Suspended Solids (w/w) | 8.64 | 3.56 | 1.83 |
| Pre-Treatment Oil (as w/w % dry basis of Whole Stillage) | 1.53 | 0.77 | 0.68 |

TABLE 9

Ethanol Fermentation using Stickwater prepared from Whole Stillage, Filtered Whole Stillage and Thin Stillage.

| | Stickwater Source | | |
|---|---|---|---|
| | Whole Stillage | Thick Stillage | Thin Stillage |
| Dextrose Utilized (g/l) | 181.5 | 173.1 | 190.7 |
| Ethanol yield (g/g dextrose utilized) | 0.430 | 0.455 | 0.435 |
| % of Theoretical Yield | 84.1% | 89.0% | 85.1% |

What is claimed is:

1. A method of hydrothermally fractionating stillage, including the steps of:

heating the stillage obtained from corn ethanol fermentation to a temperature of 250 degrees F. to 350 degrees F.;

separating the heated treated stillage into a ProFat fraction and a stickwater fraction; recovering the stickwater fraction from the heat treated stillage;

recycling all or a portion of the stickwater fraction to a fermentation process; and enhancing fermentation through the addition of the recycled stickwater fraction.

2. The method of claim 1, wherein said heating step is further defined as heating the stillage to a temperature of 280 degrees F. to 320 degrees F.

3. The method of claim 1, wherein said heating step is further defined as holding the stillage at the temperature for 3 to 60 minutes.

4. The method of claim 1, further including a step of recovering a ProFat fraction from the heat treated stillage.

5. The method of claim 1, further including a separating step chosen from the group consisting of separating protein meal and fat from ProFat; separating protein meal from ProFat; separating oil from stickwater; separating oil from protein meal; separating stickwater from protein meal; simultaneously separating oil, protein meal, and stickwater; and combinations thereof.

6. The method of claim 5, further including prior to said separating step, a step of cooling the stillage to a temperature of less than 250 degrees F.

7. The method of claim 5, further including a step chosen from the group consisting of filtering at least a portion of the stickwater fraction with membranes, concentrating at least a portion of the stickwater fraction, adding agents to at least a portion of the stickwater fraction to precipitate components, and treating at least a portion of the stickwater fraction to remove fermentation inhibitors.

8. The method of claim 5, further including the steps of adding an organism chosen from the group consisting of algae, fungus, and microorganisms to the stickwater fraction; using the stickwater fraction as a growth media; and recovering biomass, bio-products, extracts, metabolites, and treated water.

9. The method of claim 1, further including a step of removing large solids from the stillage and obtaining a large solid wet cake and thick stillage before said heating step, wherein the thick stillage consists essentially of 4 to 8% suspended solids.

10. The method of claim 1, wherein the stillage is thin stillage having 4% or less suspended solids.

11. The method of claim 1, further including the step of concentrating the stillage prior to said heating step.

12. A method of performing ethanol fermentation, including the steps of:

hydrothermally fractionating stillage obtained from corn ethanol fermentation by heating the stillage to a temperature of 250 degrees F. to 350 degrees F.;

separating the stillage into a ProFat fraction and a stickwater fraction;

recovering oil from the ProFat fraction;

recycling all or a portion of the stickwater fraction to a fermentation process; and enhancing fermentation through the addition of the recycled stickwater fraction.

13. The method of claim 12, further including prior to said hydrothermal fractionation step, the step of concentrating the stillage.

14. A method of performing ethanol fermentation, including the steps of:

separating whole stillage obtained from corn ethanol fermentation into stillage and wet cake;

hydrothermally fractionating the stillage by heating the stillage to a temperature of 250 degrees F. to 350 degrees F.;

separating the stillage into ProFat and stickwater fractions; recovering oil;

recovering a first stickwater fraction and a ProFat fraction;

dewatering the ProFat fraction, thereby obtaining a dewatered ProFat fraction and a second stickwater fraction, and adding the second stickwater fraction to the first stickwater fraction; and further processing the first and second stickwater fractions by a process selected from the group including biological processing and chemical processing, using the first and second stickwater fractions as growth media in said processing step and enhancing growth through the addition of the stickwater fraction.

15. The method of claim 14, further including before said separating whole stillage step, the steps of: cooking, fermenting, and distilling corn and obtaining ethanol; and, after said further processing step, further including the steps of recovering biomass, bio-products, extracts, and treated water from the growth media, recycling treated water; and drying the ProFat and obtaining dried distillers grains.

* * * * *